(12) United States Patent
Ziegler

(10) Patent No.: US 6,652,810 B1
(45) Date of Patent: Nov. 25, 2003

(54) MEASURING CHAMBER WITH LUMINESCENCE-OPTICAL SENSOR ELEMENTS

(75) Inventor: Werner Ziegler, Graz (AT)

(73) Assignee: F. Hoffmann la Roche AG, Basel (CH)

( * ) Notice: Subject to any disclaimer, the term of this patent is extended or adjusted under 35 U.S.C. 154(b) by 353 days.

(21) Appl. No.: 09/722,343

(22) Filed: Nov. 28, 2000

(30) Foreign Application Priority Data

Dec. 2, 1999 (AT) .............................................. 2028/99

(51) Int. Cl.[7] .............................................. G01N 21/64
(52) U.S. Cl. .............................. 422/82.08; 422/82.05; 422/68.1; 436/172; 436/164
(58) Field of Search ............... 422/82.08, 83, 422/82.05, 55, 50, 58, 68.1, 82.06, 82.07, 82.09; 436/164, 172

(56) References Cited

U.S. PATENT DOCUMENTS 5,351,563 A   10/1994   Karpf et al.
6,100,541 A * 8/2000   Nagle et al. ................. 250/573

FOREIGN PATENT DOCUMENTS

| AT | 383684  | 8/1987  |
|----|---------|---------|
| EP | 0120715 | 10/1984 |
| EP | 354895  | 2/1990  |
| EP | 0460343 | 12/1991 |
| EP | 793090  | 2/1997  |

OTHER PUBLICATIONS

M.J.P. Leiner, "Optical Sensors for In Vitro Blood Gas Analysis" in Sensors and Actuators B29 (1995), pp. 169–173.

* cited by examiner

Primary Examiner—Jill Warden
Assistant Examiner—Sam P. Siefke
(74) Attorney, Agent, or Firm—Dykema Gossett PLLC

(57) ABSTRACT

A measuring chamber such as a flow-through chamber includes a bottom part and a top part which are at least partially transparent to the excitation and measuring radiation and together form a measuring channel, and luminescence-optical sensor elements positioned in a sensing area. The bottom part and the top part each are provided with a longitudinal groove, together constituting the measuring channel. The sensor elements are placed in the longitudinal grooves of the bottom part and the top part, each of which elements is coated with an optical cover layer covering the entire sensing area.

20 Claims, 3 Drawing Sheets

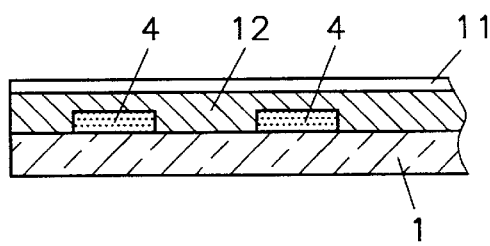
Fig.4
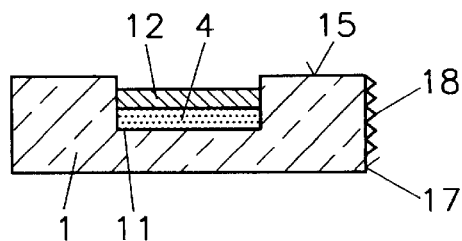
Fig.5
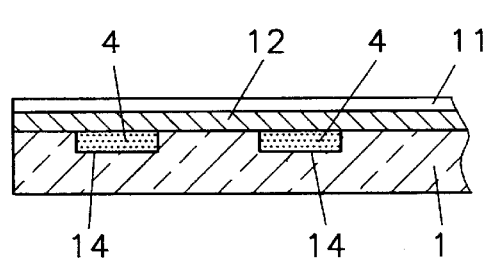
Fig.6
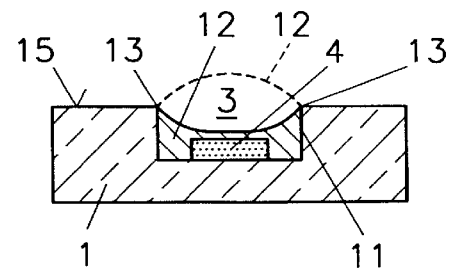
Fig.7
Fig.12
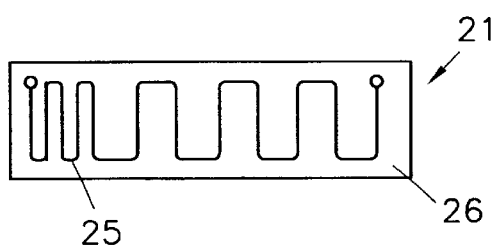
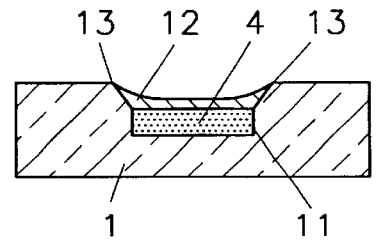
Fig.8
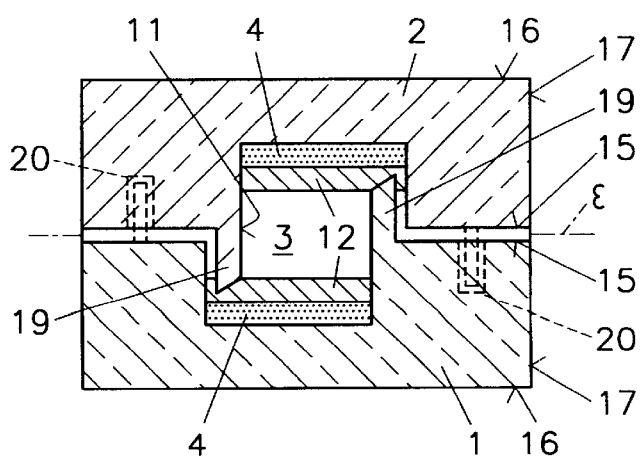
Fig.9

MEASURING CHAMBER WITH LUMINESCENCE-OPTICAL SENSOR ELEMENTS

BACKGROUND OF THE INVENTION

The invention relates to a measuring chamber, preferably a flow-through chamber comprising a bottom part and a top part which are at least partially transparent to the excitation and measuring radiation and together form a measuring channel, with luminescence-optical sensor elements provided in a sensing area.

DESCRIPTION OF PRIOR ART

Such measuring chambers are used for simultaneously measuring several parameters in liquid or gaseous samples which are introduced into the measuring chamber, or, in the instance of flow-through chambers, delivered by means of suitable pumping or suction devices. In M. J. P. LEINER, Sensors and Actuators B29 (1995) 169–173, for example, a measuring chamber for simultaneously determining pH, $PCO_2$ and $PO_2$ in blood is described under the title of "Optical sensors for in vitro blood gas analysis", the measuring chamber being configured as a flow-through cell. This cell essentially consists of two injection-molded parts made of plastic material that is transparent to the excitation and measuring radiation emitted by the luminescence-optical sensors used. Fittings for connection of sample inlet and outlet are integrated at the two ends of the measuring cell. The bottom part of the cell has three cylindrical cavities for the sensor elements in a sensing area. The top part of the measuring cell contains a groove-shaped cavity which together with the bottom part forms the measuring channel with a sample volume of about 40 $\mu l$. Two-armed light guides directed towards the bottom part of the measuring chamber are provided for excitation of the luminescence indicator in the individual luminescence-optical sensor elements and for detection of the luminescence radiation.

A halogen light source constitutes the excitation source, the required wavelengths being obtained with the use of suitable filters. The luminescence radiation emitted by the individual sensor elements is transmitted via separate light guides and cut-off filters to detectors which are connected to the evaluation unit. The measuring chamber is configured as a disposable measuring cell and is inserted for measurement into a temperature-controlled measuring device at a constant temperature of 37°. The sensor elements, which have the shape of small disks and are built in layers, consist of an adhesive layer, a transparent carrier layer, a sensing layer and an optical cover layer, as seen in the direction of the measuring channel. The optical cover layer or isolation layer serves to protect the indicator layer of the sensor against stray light from the sample or the environment (such as natural fluorescence or ambient light), thus optically decoupling the sensor elements. After the individual sensor elements have been inserted into the cylindrical cavities in the bottom part, the two parts of the measuring chamber are glued together. Due to the different kinds of materials encountered by the sample in the measuring channel, troubles may arise upon filling the measuring channel, since different materials, such as the wall of the measuring cell and the optical cover layer, will not be uniformly wetted by the sample, which may lead to air bubbles or non-homogeneous flow conditions. As a consequence, the sample may flow around the sides of the sensor element.

Another disposable measuring element for simultaneously measuring a plurality of different sample components is described in EP 0 354 895 B1, which comprises a sensor part and a sampling part connected thereto. The sensor part is provided with a continuous sample channel containing several sensor elements. Excitation of the sensor elements and detection of the measuring radiation takes place via light guides which are guided to the transparent sensor part from outside.

SUMMARY OF THE INVENTION

It is the object of the present invention to propose a measuring chamber on the basis of the above state of the art, which should be simple and inexpensive to produce, featuring homogeneous flow conditions in the measuring channel and permitting a greater number of individual parameters to be determined while using essentially the same sample volume as before.

According to the invention this object is achieved by providing a longitudinal groove each in the bottom part and in the top part, which grooves together form the measuring channel, and by arranging for sensor elements to be placed in the longitudinal grooves of the bottom part and the top part, each of which elements is coated with an optical cover layer covering the entire sensing area. These provisions of the invention will allow the number of luminescence-optical sensor elements to be doubled while the sample volume will essentially remain the same, as the sensor elements will be positioned in the bottom part as well as in the top part. Since the longitudinal groove is provided with a continuous optical cover layer covering the entire sensing area in the bottom part as well as in the top part, the two cover layers will form a shallow sample channel or capillary gap, in which the sample will be able to pass through the measuring channel without developing air bubbles or forming undesirable flow profiles.

It will be of special advantage to extend the optical cover layer in the bottom and top parts up to the two edges of the longitudinal groove, thus forming a homogeneous lining of the measuring channel.

According to a preferred variant a plurality of sensor elements could be assembled to form a group. Groups of one and the same kind of sensor elements may be employed to obtain a mean value from a number of individual measurements, for instance.

The individual sensor elements may be positioned in cavities at the bottom of the longitudinal groove and covered by a continuous optical cover layer.

In a further variant of the invention the proposal is put forward that the optical cover layer extend into the areas between adjacent sensor elements to optically decouple adjacent sensor elements in these areas.

According to another variant offering special advantages, the bottom part and the top part of the measuring chamber are configured as essentially symmetrical parts, and are provided with inner surfaces facing each other and containing the longitudinal groove holding the sensor elements, and outer surfaces parallel to the inner surfaces, and lateral surfaces essentially normal to the outer surfaces. As opposed to state-of-the-art measuring chambers manufacturing, will be considerably facilitated if the bottom and top parts of the measuring chamber are injection-molded parts of identical design which can be provided with different sensor elements or groups of sensor elements. This design will permit the use of sensor elements for pH, $PCO_2$ and $PO_2$ measurement in the bottom part, and combining of the bottom part with a top part carrying sensor elements for determining different electrolytes, such as sodium, potassium and calcium. On the other hands the bottom part measuring the blood gas parameters pH, $PO_2$ and $PCO_2$, can be combined with a top part carrying biosensors for determining lactate, glucose, urea, creatinine, etc. The advantage is that individual parts of the measuring chamber may be provided with a group of sensor elements, and that such parts can be assembled on account of their symmetry to form different types of measuring chambers, depending on the parameters desired.

According to the invention such symmetrical parts of a measuring chamber, essentially in the shape of a parallel epiped, will permit optical excitation of the individual sensor elements via the lateral faces, and detection of the measuring radiation via the outer faces of the symmetrical parts. In this way the excitation light is optically decoupled from the measuring light at an early stage, i.e., in the respective part of the measuring chamber. The general principle of optical separation of excitation radiation and measuring radiation in a transparent carrier element is described in AT 383 684 B. That description proposes a carrier element with parallel boundary faces (comparable to the bottom and top part of this invention), which is provided with a sensor layer on one of these faces, the sensor layer being subject to excitation light from a radiation source. The light from the radiation source is incident on the sensor layer through an aperture, the measuring radiation generated in this way being directed essentially normally to the direction of the excitation radiation, towards a detector positioned at a face on the lateral wall of the carrier element. Light guidance in the carrier element is essentially due to total reflection of the measuring radiation at the boundary faces of the carrier element. This principle is reversible, i.e, excitation may take place via the lateral surface and detection via the surface parallel to the sensor face.

It is of special advantage to arrange the sensor elements of the bottom part and the top part in opposing pairs. In this way a laterally placed light source may be used to subject two sensor elements each to excitation radiation, whose measuring radiation is detected via the outer face of the bottom part and the outer face of the top part. The measuring radiation of the two sensor elements is optically decoupled via the two optical cover layers lining the measuring channel.

In order to prevent mutual optical influences between the sensor elements positioned side by side in the bottom or top part, they may be individually contacted with optical waveguides. Another possibility would be to take optical or electronic measures as described in EP 0 793 090 A1.

To improve the coupling-in of excitation light into the bottom and/or top part of the measuring chamber it is proposed for each sensor element to provide at least one lateral surface of a measuring chamber part with an optical element, preferably a collimating lens, a Fresnel lens or a grating, which will couple in or focus the excitation radiation in the direction of the sensor elements.

The measuring chamber according to the invention can be thermostatted in a simple way, by providing a heatable foil between the bottom part and the top part, which should extend into the measuring channel. Contrary to state-of-the-art designs it will not be necessary to overcome the heat-insulating effect of the wall of the measuring chamber for thermostatting the sample, since all sensor elements are temperature-controlled in the same way directly inside the measuring channel by utilizing the good thermal conductivity of the aqueous sample.

Preferably, the heatable foil may be provided with an electrically conductive layer in the shape of a meandering strip conductor.

In further development of the invention a separating foil may be provided between the bottom part and the top part, which will divide the measuring channel into two separate partial channels. This will permit the measuring of a calibrating medium or quality control means in one partial channel of the measuring chamber, while the sample components are being detected in the other partial channel at the same time. In this application one and the same kind of sensor elements are preferably arranged in opposing pairs and subjected to excitation radiation from the same light source.

It will further be possible to use the separating foil simultaneously as heating foil for temperature control of the measuring chamber.

BRIEF DESCRIPTION OF THE DRAWINGS

The invention is explained below in more detail with reference to the accompanying drawing, wherein

FIG. 4 is a section along line IV—IV in FIG. 2;

FIG. 5 is a section along line V—V in FIG. 2;

FIGS. 6 and 7 show different variants of the measuring chamber, the sectional view corresponding to that in FIGS. 4 and 5, respectively;

FIG. 8 shows a variant in a sectional representation as in FIG. 5;

FIGS. 9 and 10 show further variants of the measuring chamber, the sectional representation corresponding *to that of FIG. 1;

FIG. 12 shows a detail from FIG. 11;

DETAILED DESCRIPTION OF THE PREFERRED EMBODIMENTS

Figure 1:
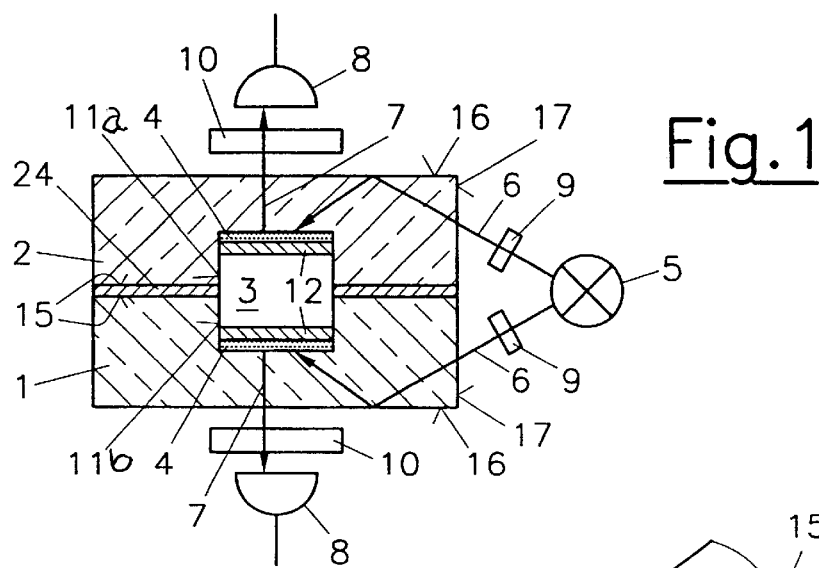
FIG. 1 is a representation of a measuring chamber according to the invention in a section normal to the axis of the measuring chamber.

The measuring chamber presented in FIG. 1 comprises a transparent bottom part 1 and a transparent top part 2, which together form a measuring channel 3. A sectional view of the measuring chamber is given in FIG. 1, the cutting plane going through the luminescence-optical sensor elements 4 in the measuring channel 3 and being normal to the axis of the measuring channel 3. The sensor elements 4 are subject to excitation radiation 6 from the light source 5, and the measuring radiation 7 emitted in dependence on the sample parameters is detected by suitable detectors 8. In the path of the excitation radiation 6 and the measuring radiation 7 excitation filters 9 and measuring filters 10 may be provided. The bottom part 1 and the top part 2 are provided with a respective longitudinal grooves 11a and 11b, which will constitute the measuring channel 3 upon assembly of the two parts 1, 2 of the measuring chamber. Utilizing the volume of the measuring channel in the best possible way, sensor elements 4 are positioned in the longitudinal grooves of both bottom part 1 and top part 2, which elements 4 are coated with a continuous optical cover layer 12 covering the entire sensing area. In this way a homogeneous lining of the measuring channel 3 is obtained and troublefree filling of the measuring channel 3 is ensured.

The optical cover layer 12 covering the sensing area has the following properties which may be optimized to suit the respective application.

Geometrical Properties of the Measuring Chamber

The channel cross-section, which will determine the flow and filling characteristics of the measuring channel 3, may assume different shapes depending on the manner in which the optical cover layer is configured. For example, the cross-section may take the form of a rectangle with optional side ratio, extending as far as to the capillary gap, whose corners may be rounded. In addition, lenticular (see FIG. 7), elliptical or circular cross-sections may be chosen. Such cross-sections may be obtained by means of a blade, an insulating material of suitable viscosity being required for the cover layer. It is essential that the measuring channel should have the same width over its entire length (at least in the sensing area) and thus the same flow cross-section if a continuous, homogeneous coating is provided.

The optical cover layer 12 may also be applied by dispensing, provided the material is sufficiently flowable and suitable masks are employed. This method is preferably used if the sensor elements are positioned in cavities of the longitudinal groove 11 (see FIG. 6), or are to be enclosed by the cover layer 12 on all sides. It would further be possible to apply the cover layer 12 by dabber printing, whereby the printing process is repeated until the desired cover thickness has been achieved.

Chemical and Physical Properties of the Cover Layer

By selecting a suitable material for the cover layer , such as silicone, hydrogel, polystyrene, polyvinyl chloride with plasticizers, etc., desirable properties may be optimized to suit the respective application as following:

wetting by the sample (blood, serum, plasma, etc.) and by control and calibration liquids Gas diffusion, vapour diffusion Permeability to liquids and gases Permeability to protons Ability to store fluids.

Optical Properties of the Cover Layer

By the addition of filling agents whose types, colours, concentrations are variable, the optical properties of the cover layer may be adapted to the measuring situation. It is important to suppress radiation from the sample (ambient light, natural fluoresence) and to provide for the so-called optical decoupling between sample and sensor element. In the areas between the individual sensor elements the optical cover layer makes sure that the individual sensor elements are optically decoupled. Adding a black filler (carbon black), for example, will help to absorb light that may otherwise propagate between two adjacent sensor elements.

It should be understood that in all figures the height of the measuring channel 3 and the thickness of the sensor layer 4 and the optical cover layer 12 are exaggerated for better illustration, and that the actual measuring channel 3 may be configured as a shallow gap (capillary gap) between the two optical cover layers 12.

Figure 2:
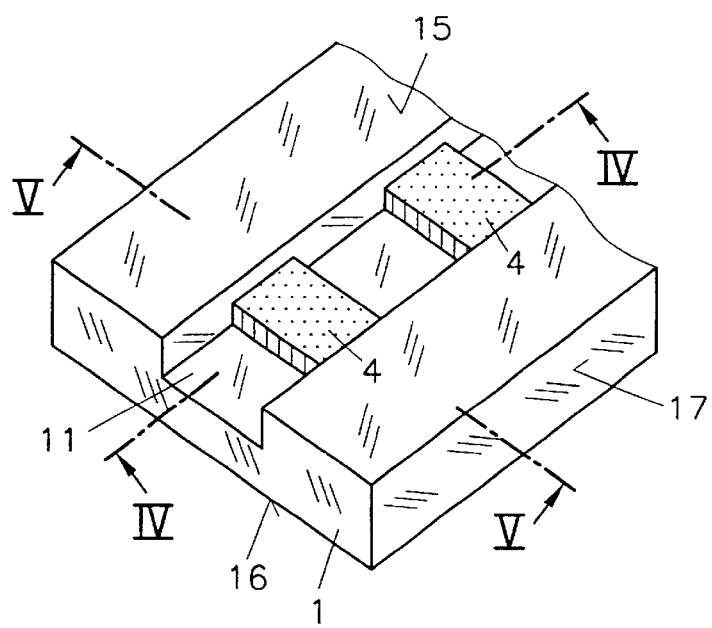
FIG. 2 is a perspective view of the bottom part of the measuring chamber in FIG. 1.

FIG. 2 shows the. bottom part 2 of the measuring chamber according to FIG. 1 in a three-dimensional view, the cover layer on top of the sensor elements 4 in the longitudinal groove 11 having been omitted for better view.

Figure 3A:
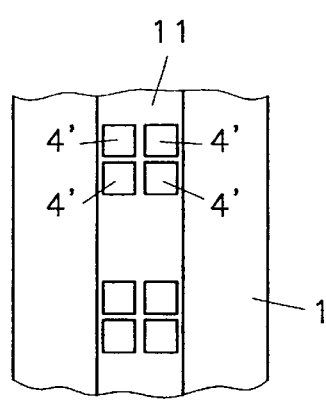
FIGS. 3a and 3b each show a variant of the bottom part of the measuring chamber as seen from above.
Figure 3B:
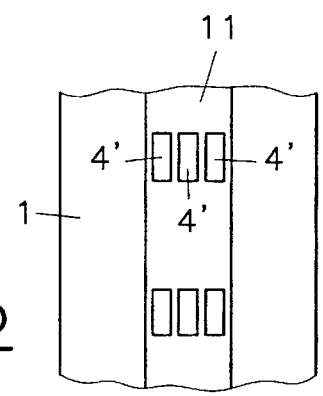

FIGS. 3a and 3b each give a view of the bottom part 1 of a measuring chamber from above, the variant in FIG. 3a showing the longitudinal groove 11 with four sensor elements 4' each combined in a group. A similar arrangement is presented in FIG. 3b, where three strip-like sensor elements 4' each are combined to form a group. Such sensor groups can be detected with the use of imaging detector systems, such as CCD cameras.

Further applications of the optical cover layer 12 are shown in the sectional representations of FIG. 4 to FIG. 8, the layer shown in FIG. 4 extending into the areas between adjacent sensor elements 4 and ensuring optical decoupling of adjacent sensor elements. According to the variant of FIG. 6 the sensor elements 4 could also be positioned in cavities 14 in the bottom of the longitudinal groove 11, the common optical cover layer ensuring a homogenous surface in this instance, too.

If, as shown in FIG. 7, the optical cover layer 12 is extended up to the two edges 13 of the longitudinal groove 11, and a similar configuration is selected for the top part not shown in this drawing (see dotted line 12), a homogeneous lining is achieved with the material of the optical cover layer 12 for the entire lenticular cross-section of the measuring channel. Additionally, the sensor elements 4 may be given a diameter of less than the width of the longitudinal groove 11, so that the cover layer 12 will also cover the sides of the sensor elements 4 and optically decouple them.

FIG. 8 shows a sectional representation of the measuring chamber where the longitudinal groove has a sloping wall towards the measuring channel, the cover layer 12 again extending up to the groove edges 13. In this manner a shallow measuring channel with good flow properties is obtained.

As can be seen from the different variants of the invention, the two parts of the measuring chamber, i.e., bottom part 1 and top part 2, may be completely identical and/or centrally symmetrical relative to the axis of the measuring chamber, so that the same injection mold can be used for manufacturing both parts. The individual parts feature inner faces 15 facing each other, outer faces 16 parallel thereto, and lateral faces 17 that are essentially normal to the outer faces 16. The longitudinal groove 11 is formed on the inner face 15. Optical excitation of the individual sensor elements 4 may be effected via the lateral faces 17 of parts 1, 2 of the measuring chamber, the excitation radiation 6 being passed to the sensor elements 4 by total reflection between the inner and outer faces 15, 16, which are plane-parallel to each other. In the area of the sensor elements 4 the total reflection is cancelled by matching the refraction indices, which will permit the excitation radiation to enter the sensor layer of the sensor elements 4. The luminescence radiation 7 emitted by the sensor elements is measured essentially normal to the direction of the excitation radiation by means of the detectors 8 provided on the outer faces 16.

To improve coupling-in of the excitation radiation and focusing of the excitation radiation onto the sensor elements 4, an optical element 18, such as a collimating lens (see FIG. 10) or a Fresnel lens or a grating (see FIG. 5) may be positioned or integrally molded with one of the lateral faces 17 of each part 1, 2 of the measuring chamber. It is possible, for example, to integrate such optical elements 18 on the side faces 17 of parts 1, 2 by an injection-molding process.

FIG. 9 presents a variant of the measuring chamber according to the invention, where the longitudinal groove 11 of the bottom and top parts 1, 2 has a cutting edge 19 along one edge of the groove, which cutting edge 19 projects beyond the sealing plane ϵ and serves as a seal extending into the optical cover layer 12 on the opposite side in the assembled state of the two parts 1, 2 of the measuring chamber. In this manner a centrally symmetrical measuring chamber is obtained, the two parts 1, 2 of the measuring chamber being identical. Furthermore, locking and centering elements 20 may be provided in the bottom part 1, which lock with locking and centering elements 20 in the top part 2. On assembly of the measuring chamber, the two parts 1 and 2 will lock easily by snapping in, and the two cutting edges 19 will serve as sears as the cover layer 12 undergoes a permanently elastic deformation. Additional sealing or gluing of the two parts will not be required.

Figure 10:
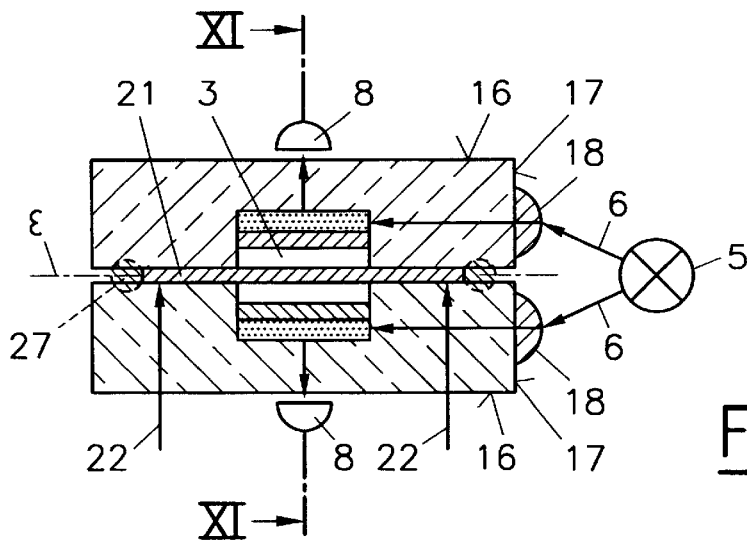
Figure 11:
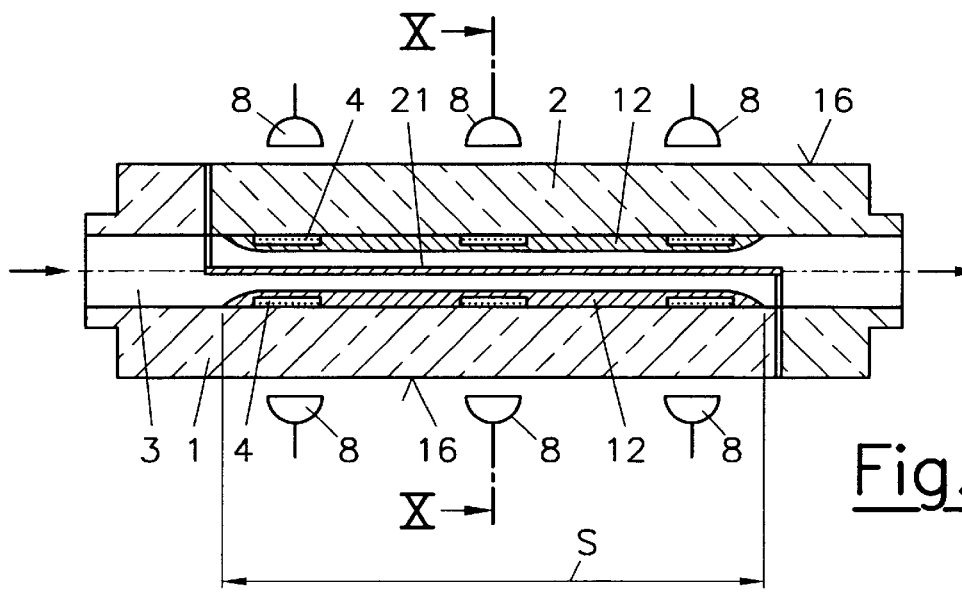
FIG. 11 is a measuring chamber as in FIG. 10, in a longitudinal section.

In FIGS. 10 and 11 (see section along line XI—XI in FIG. 10 and line X—X in FIG. 11) a variant of the measuring chamber is shown, which is provided with a heatable foil 21 between the bottom part 1 and the top part 2 and extending into the measuring channel 3 for temperature control of the measuring chamber. The electrical connections 22 for the heatable foil 21 could also leave the side of the measuring chamber in the sealing plane 8. According to FIG. 12 the heatable foil 21 may be applied on a carrier foil 26 taking the form of a meandering strip conductor 25. Due to a specific design of the strip conductors (width, shape, distance between the individual conductors) local heating performance may be tailored to meet specific demands. In the entrance area of the sample, for instance, more heat will be required in order to (pre)heat the sample quickly.

If several sensor elements are placed in a part of the measuring chamber (see FIG. 11; three sensor elements each in bottom part 1 and top part 2) the measuring radiation coming from the individual sensor elements of each part must be unambiguously assigned to the individual sensor elements. For this purpose optical separators as well as electronic or mathematial means in the evaluation unit as disclosed in EP 0 793 090 A1, for example, may be employed. It should be noted in this case that both excitation and evaluation may be pulsed in time, or that the excitation radiation and measuring radiation may be modulated and demodulated accordingly. Within the measuring chamber the sensing area S at least is covered by the continuous cover layer 12.

Figure 13:
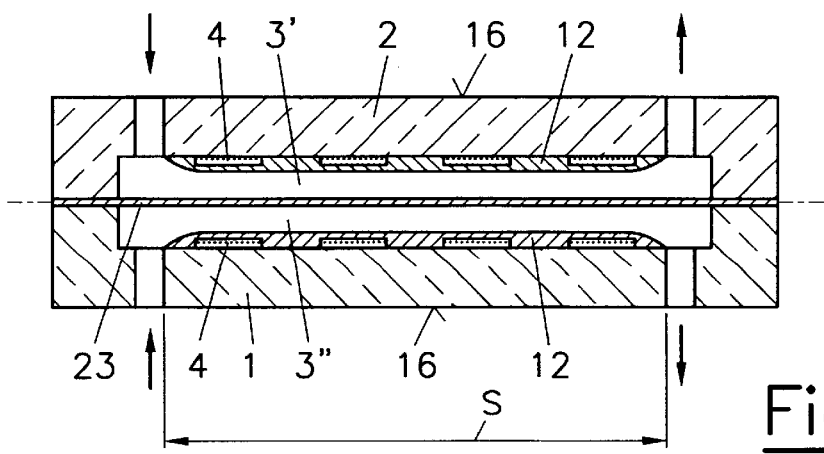
FIG. 13 shows yet another variant of the measuring chamber in a longitudinal section.

According to the variant of FIG. 13 a separating foil 23 may be provided between the bottom part 1 and the top part 2, which will divide the measuring channel 3 into two partial channels 3', 3". With this kind of measuring chamber the first partial channel 3' is used for measuring a sample while the second partial channel 3" is used at the same time for measuring a calibrating or reference medium. If the same kinds of sensor elements 4 are positioned opposite of each other, both can be excited by means of the same light source (see excitation geometry according to FIG. 10), and intensity fluctuations of the light source will have no influence on the ratio of sample signal to reference signal.

Besides the method of joining bottom part 1 and top part 2 by a snap-on connection (see FIG. 9), they may also be welded (e.g. ultrasonic welding) or glued together to provide a fluid-tight connection (see adhesive layer or double-face adhesive film 24 according to FIG. 1). In addition, a sealing element 27 may be provided between the bottom part 1 and the top part 2 (FIG. 10).

Following are examples of suitable dimensions and materials for use, which will not restrict the invention in any way.

Materials for the two Parts of the Measuring Chamber

| | |
|---|---|
| PC | polycarbonate |
| PMMA | polymethyl methacrylate |
| COC | cyclooletin copolymer |
| PS | polystyrene |
| PMP | polymethyl pentene |
| | polyacrylate |

Materials for the Heating Foil

Pure metal foil, such as aluminum or gold

Metal foil with thin coating of a polymer, preferably the same material as for the optical cover layer Carrier foil (Mylar, Captone) printed with electrically conducting layer, preferably configured as strip conductors Carrier foil with a metal oxide layer, such as ITO (indium-tin-oxide), applied by sputtering.

Dimensions of the Measuring Chamber

Number of sensors: 2–7 sensors in bank-type arrangement for each longitudinal groove 11, and preferably 3–5 sensors in a bank Area per sensor: 2–30 square millimeters, and preferably 4–16 square millimeters Width of channel: 2–10 mm, and preferably 3–5 mm Effective height of channel: 0.08–0.2 mm, and preferably 0.1–0.15 mm Thickness of cover layer: 5–200 $\mu$m, and preferably 10–50 $\mu$m Distance sensor-sensor: >3 mm, and preferably 4–5 mm Volume of Measuring Channel Small Measuring Chamber:

3 sensors at 3×3 squ.mm each in both bottom and top part distance between sensors 3 mm channel length before and after sensors 5 mm total channel length 25 mm, channel width 3 mm, channel height 0.1 mm filling volume 7.5 $\mu$l Medium-size Measuring Chamber:

4 sensors at 4×3 squ.mm each in both bottom and top part distance between sensors 4 mm, distance sensor-channel edge 0.5 mm channel length before and after sensors about 7 mm total channel length 42 mm, channel width 4 mm, channel height 0.15 mm filling volume 25 $\mu$l Large Measuring Chamber:

6 sensors at 5×5 squ.mm each in both bottom and top part distance between sensors 5 mm, distance sensor-channel edge 0.5 mm channel length before and after sensors about 10 mm total channel length 75 mm, channel width 6 mm, channel height 0.2 mm filling volume 90 $\mu$l For application of the sensors the following techniques may be employed:

(A) If the bottom of the measuring channel is plane without cavities;

1. The sensors are prefabricated on a carrier foil and glued into place. The adhesive must be transparent. Each sensor is punched out of a sheet of carrier foil and is positioned individually.
2. The individual sensors are prefabricated on a strip of foil in the shape of the measuring channel. Preferably, these sensor arrays are cut in strips from a long tape of foil, transversely to the longitudinal direction. On this foil tape the sensitive layers are applied longitudinally as narrow continuous strips. The continuous optical cover layer may be applied before or after the sensor strip is glued into the sample channel.
3. Dabber printing: The sensor layer is applied in one or several printing steps. Multilayer sensors will yield a larger signal but have a longer response time.
4. Use of & mask (i.e., a self-adhesive polymer film with openings in the sensor positions), which is removed after coating. Into the cavities formed by the mask the sensors are applied by means of dispensing or ink-jet techniques.

(B) If the measuring channel is provided with cavities for holding the sensors;
1. Dispensing the sensor material.
2. Using ink-jet techniques
3. Gluing the sensors, which are prefabricated on a carrier foil, into place.

What is claimed is:

1. Measuring chamber comprising a bottom part and a top part, which are at least partially transparent for excitation and measuring radiation, and a measuring channel, having luminescence-optical sensor elements provided in a sensing area, wherein a longitudinal groove is provided each in said bottom part and in said top part, which together form said measuring channel, and wherein said luminescence-optical sensor elements are placed in said longitudinal groove of said bottom part and in said longitudinal groove of said top part, each of said luminescence-optical sensor elements is coated with an optical cover layer covering said sensing area.

2. Measuring chamber according to claim 1, wherein said measuring chamber is a flow-through chamber.

3. Measuring chamber according to claim 1, wherein said luminescence-optical sensor elements are positioned in cavities at bottom bottoms of said longitudinal grooves.

4. Measuring chamber according to claim 1, wherein a plurality of said luminescence-optical sensor elements are assembled to form a group.

5. Measuring chamber according to claim 1, wherein said optical cover layer extends into areas between adjacent luminescence-optical sensor elements to optically decouple adjacent sensor elements in said areas.

6. Measuring chamber according to claim 1, wherein said luminescence-optical sensor elements of said bottom part and said top part are arranged as opposing pairs.

7. Measuring chamber according to claim 1, wherein said optical cover layer is extended in said bottom and said top parts up to both edges of said longitudinal grooves, thus forming a homogeneous lining of said measuring channel.

8. Measuring chamber according to claim 1, wherein said bottom part and said top part of said measuring chamber are configured as essentially symmetrical parts, and are provided with inner surfaces facing each other and containing said longitudinal grooves holding said luminescence-optical sensor elements, outer surfaces parallel to said inner surfaces, and lateral surfaces essentially normal to said outer surfaces.

9. Measuring chamber according to claim 8, wherein said lateral surfaces are provided for optical excitation of said individual sensor elements and said outer surfaces are provided for detection of said measuring radiation.

10. Measuring chamber according to claim 8, wherein for each of said luminescence-optical sensor elements at least one of said lateral surfaces of said bottom and top parts is provided with an optical element for coupling in or focusing said excitation radiation in a direction of said luminescence-optical sensor elements.

11. Measuring chamber according to claim 10, wherein said optical element is a collimating lens.

12. Measuring chamber according to claim 10, wherein said optical element is a Fresnel lens.

13. Measuring chamber according to claim 10, wherein said optical element is a grating.

14. Measuring chamber according to claim 1, wherein a heatable foil is provided between said bottom part and said top part, which extends into said measuring channel for temperature-control of said measuring chamber.

15. Measuring chamber according to claim 14, wherein said heatable foil is provided with an electrically conductive layer in shape of a meandering strip conductor.

16. Measuring chamber according to claim 1, wherein a separating foil is provided between said bottom part and said top part, said separating foil dividing said measuring channel into two separate partial channels.

17. Measuring chamber according to claim 1, wherein a fluid-tight connection between said bottom part and said top part is established by gluing or welding.

18. Measuring chamber according to claim 1, wherein said bottom part is provided with locking and centering elements, which lock with locking and centering elements arranged centrally symmetrically in said top part.

19. Measuring chamber according to claim 18, wherein a sealing element is provided between said bottom part and said top part.

20. Measuring chamber according to claim 18, wherein said longitudinal grooves of said bottom and top parts have cutting edges along one edge of said longitudinal grooves, wherein each cutting edge projects beyond a sealing plane $\epsilon$ and serves as a seal extending into said optical cover layer on the opposite side in an assembled state of said bottom and top parts of said measuring chamber.

* * * * *